US006598627B2

(12) United States Patent
Manzari et al.

(10) Patent No.: US 6,598,627 B2
(45) Date of Patent: Jul. 29, 2003

(54) APPARATUS SUITABLE FOR PREPARING A CUSTOM PERSONAL CARE COMPOSITION

(75) Inventors: Kenneth Paul Manzari, West Haven, CT (US); Walter Anthony Biercevicz, Prospect, CT (US); Walter Stoeckman, Mahopac, NY (US); Peter Anthony Divone, Sr., Bardonia, NY (US); Christy A. Bridges, Fairfield, CT (US); Kevin Keating, Darien, CT (US); Robert Avena, New York, NY (US)

(73) Assignee: Unilever Home & Personal Care USA, a division of Conopco, Inc., Greenwich, CT (US)

( * ) Notice: Subject to any disclaimer, the term of this patent is extended or adjusted under 35 U.S.C. 154(b) by 0 days.

(21) Appl. No.: 09/930,414

(22) Filed: Aug. 15, 2001

(65) Prior Publication Data

US 2002/0056724 A1 May 16, 2002

Related U.S. Application Data

(60) Provisional application No. 60/227,822, filed on Aug. 25, 2000.

(51) Int. Cl.⁷ ................................................. B65B 1/04
(52) U.S. Cl. .............................. 141/104; 141/94; 141/9
(58) Field of Search ................................. 700/240, 241, 700/242, 243; 141/2, 9, 18, 100–104, 72, 80, 98, 94, 95, 192, 198

(56) References Cited

U.S. PATENT DOCUMENTS

| 2,923,438 A | 2/1960 | Logan et al. |
| 3,428,218 A | 2/1969 | Coja |
| 3,915,207 A | 10/1975 | Greenfield, Jr. |
| 4,258,759 A | 3/1981 | Achen |
| 4,871,262 A | 10/1989 | Krauss et al. |
| 5,474,211 A | 12/1995 | Hellenberg |
| 5,544,684 A * | 8/1996 | Robinette, III ................ 141/83 |
| 5,622,692 A | 4/1997 | Rigg et al. |
| 5,749,652 A | 5/1998 | Brunn et al. |
| 5,903,465 A | 5/1999 | Brown |
| 5,972,322 A | 10/1999 | Rath et al. |
| 6,202,895 B1 | 3/2001 | Fox |

FOREIGN PATENT DOCUMENTS

| BE | 626 531 | 4/1963 |
| DE | 2523918 | 12/1976 |
| DE | 41 10 299 C1 | 3/1991 |
| EP | 0468703 A1 | 1/1992 |
| WO | 86/02320 | 4/1986 |
| WO | 95/28621 | 10/1995 |
| WO | 01/58238 | 8/2001 |

OTHER PUBLICATIONS

International Search Report PCT/EP 01/07907 dated Dec. 19, 2001 4 pp..

* cited by examiner

Primary Examiner—Steven O. Douglas
(74) Attorney, Agent, or Firm—Alan A. Bornstein (57) ABSTRACT

An apparatus is described for providing a customized, personal care product to a consumer at a location, typically the point of sale, that is remote from a second location in which a personal care product base composition is prepared. A selection of customizing agents of different classes with a common vehicle is made available to the consumer for custom formulation of a personal care product with the desired attributes. The apparatus typically includes a plurality of product base dispensers, a plurality of fragrance dispensers, and a plurality of customizing agent dispensers that may contain benefit agents, botanical extracts, active ingredients for skin and hair, and the like. A blank vehicle is substituted if insufficient customizing agents are selected. Efficient mixing mechanisms are also described.

13 Claims, 9 Drawing Sheets

APPARATUS SUITABLE FOR PREPARING A CUSTOM PERSONAL CARE COMPOSITION

PRIORITY

This application claims priority to provisional application No. 60/227,822 filed Aug. 25, 2000.

BACKGROUND OF THE INVENTION

Many personal care products such as body wash, facial cleansing gel, hair shampoo, hair conditioner, face lotion and other personal care products that are currently available are provided as prepared formulations. A drawback of such products is that the user cannot alter the formulation to accommodate their particular skin and hair characteristics, personal preferences, or to provide specialized treatment. A further drawback is the uncertainty of the age and freshness of the prepared formulation which may have been prepared many months or years before the product is sold.

Multiple-part product kits that contain separate components of e.g. a hair shampoo, hair conditioner, cosmetics, or other personal care products are available from many professional salons and some retail personal care outlets. However, the user is still unable to customize the individual formulations in light of the consumer's unique personal care preferences and requirements.

Therefore, one aspect of the invention is to provide an apparatus that enables a user to formulate a variety of personal care product compositions to best suit the needs of the consumer. Another aspect of the invention is to provide an apparatus that is easy to use such that the user may be a lay-person who is able formulate a customized personal care product. Another aspect of the invention is to provide an apparatus with a plurality of customizing agent dispensing stations, and a plurality of personal care product base dispensing stations designed to efficiently prepare stable personal care product which are freshly blended while the consumer waits. Another aspect of the invention is to mix the typically viscous blends of personal care products in an efficient manner.

SUMMARY OF THE INVENTION

An apparatus is provided for preparing a customized, personal care product for a consumer typically at a location remote from a second location in which a personal care product base composition is prepared. The apparatus comprises a plurality of personal care base compositions each contained in dispensing station and variants from two or more classes of customizing agents each contained in a dispensing station. The consumer is allowed to select, in any sequence, one personal care base composition and at least two variants from separate classes of customizing agents, such as a fragrance and a benefit agent. The user doses, in any sequence, the consumer selected personal care base composition, customizing agents, and, if necessary, sufficient liquid vehicle into a container, mixes the contents until uniform, and labels the container using the inventive dispensing apparatus.

A sufficient quantity of a blank composition having substantially the same vehicle composition as that of the customizing agent may be dosed in the container if an insufficient number of customizing agents are selected by the consumer. This allows for maintaining the optimum concentration of product ingredients while providing many choices for the consumer in customizing the product.

The inventive dispensing apparatus is preferably used with personal care product base compositions including cleansing and conditioning product bases useful for formulating body wash, body lotion, body mist spray, hydroalcoholic toner, facial cleansing gel, waterless cleanser, hair shampoo, hair conditioner, face lotion and the like.

BRIEF DESCRIPTION OF THE DRAWINGS

FIGS. 7A, 7B and 7C are perspective representations of one embodiment of a useful bottle holder for a mixing device for the inventive dispensing system.

DETAILED DESCRIPTION OF THE PREFERRED EMBODIMENT

Figure 1:
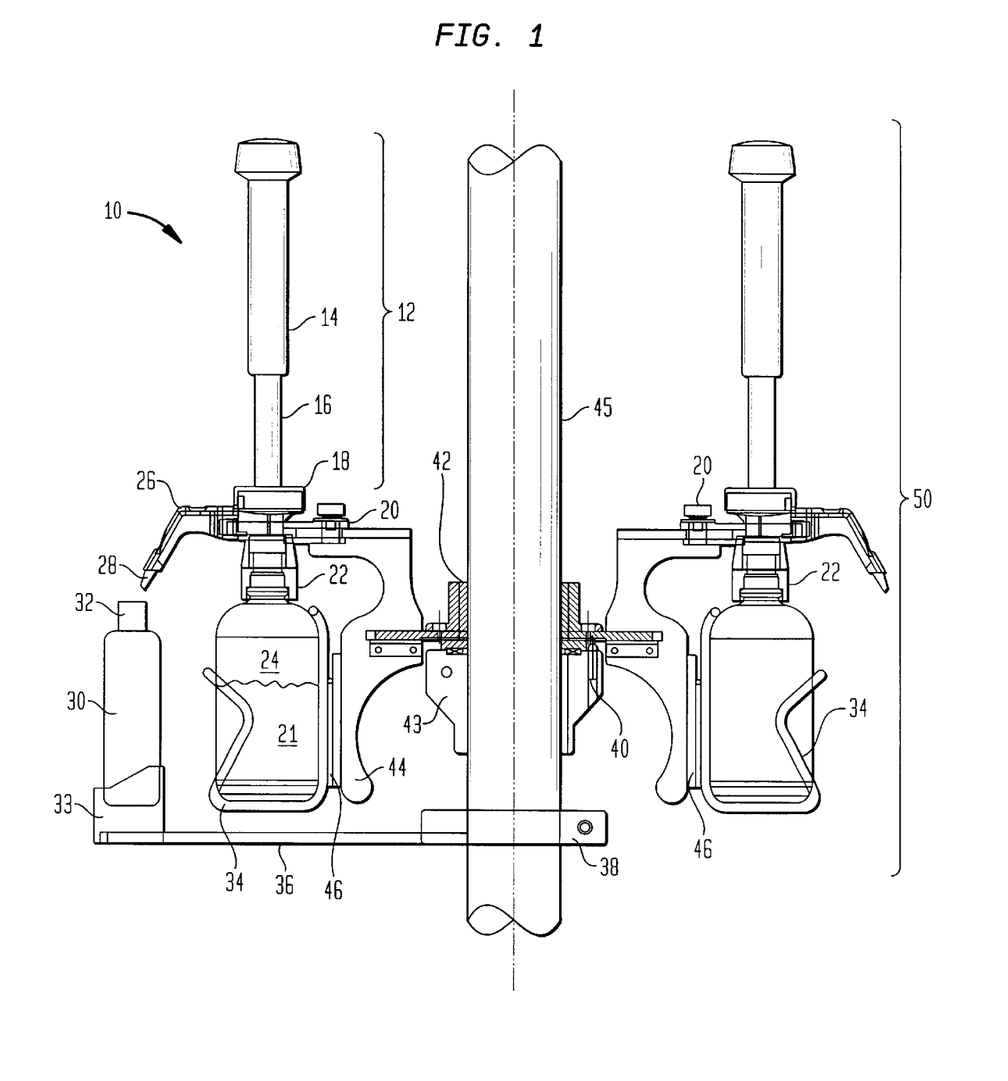
FIG. 1 is a cross sectional view of one embodiment of the inventive dispensing system having two dispensing devices positioned opposite each other.

Referring to FIG. 1, dispensing station 10 is depicted having dispensing device 12, which contains measuring device 14, pump 16 and pump head 18. Storage bottle 24 is adapted to fit dispensing device 12 by way of adapter 22. Storage bottle 24 contains customizing agent 21, which is dispensing via outlet tube 28 supported by outlet guide 26. Outlet guide 26 is removably attached to pump head 18 and is also supported by outlet positioning fixture 20 via outlet positioning fixture arms 64. Outlet positioning fixture 20 is supported at its opposite end by dispenser supporting member 44. Dispensing supporting member 44 also supports storage bottle 24 by both a direct and biasing arrangement via storage bottle holder 34, which is slidably connected to dispenser supporting member 44 via slidable mount 46. In operation, dispensing device 12 causes customizing agent 21 to be dispensed from storage bottle 24 through outlet tube 28 into consumer bottle 30 via consumer bottle neck 32. Consumer bottle 30, having consumer bottle neck 32 is supported in a fixed position relative to outlet 28 via consumer bottle holder 33 which is removably attached to one end of consumer bottle holder supporting member 36. Consumer bottle holder supporting member 36 is connected via its other end to supporting member locking ring 38. Dispenser supporting member 44 is rotatably attached to shaft 45 by way of bearing 42 and supporting ring 43. Supporting member-locking ring 38 is fixably attached to shaft 45. Detent mechanism 40 allows dispensing station 10 to be rotated reproducibly into at least one predetermined position.

Figure 1A:
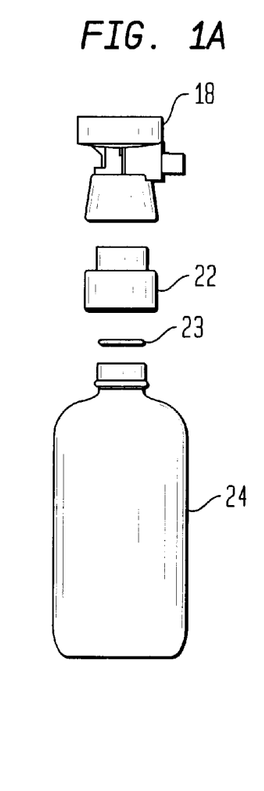
FIGS. 1A and 1B are exploded diagrams of the storage container of the embodiment illustrated in FIG. 1 with its adapter and pump head.
Figure 1B:
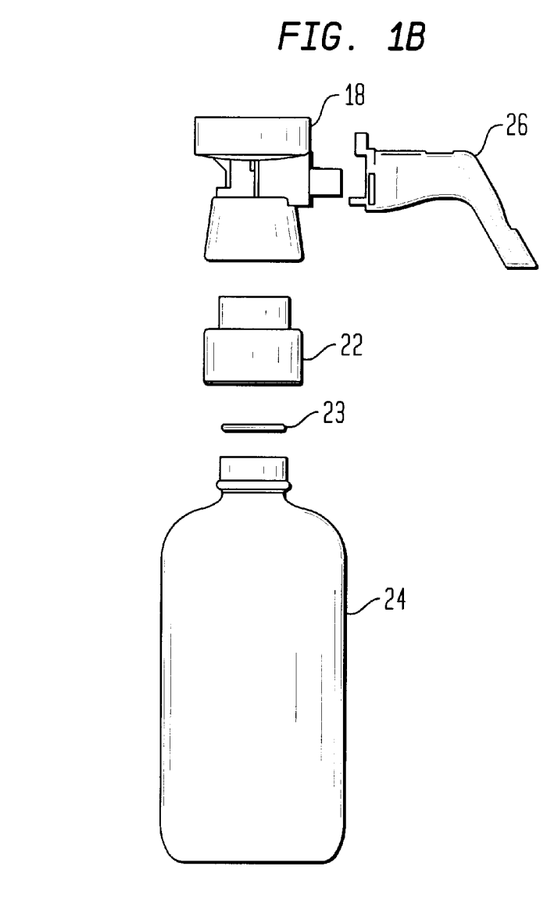
Figure 1C:
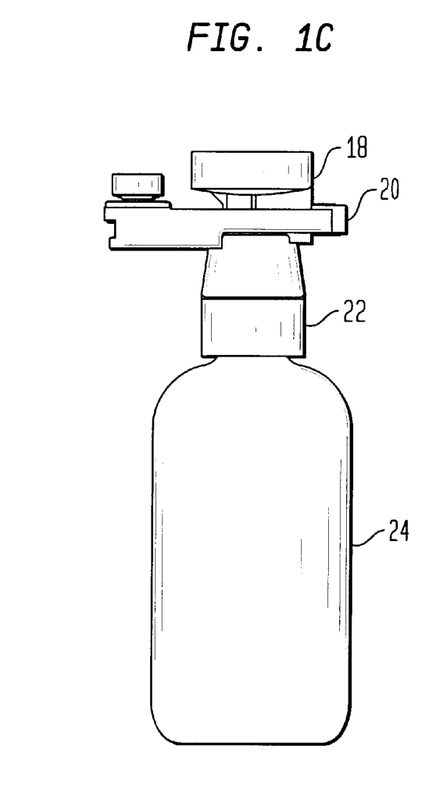
FIG. 1C is a perspective representation of the storage bottle depicted in FIGS. 1A and 1B with its outlet-positioning fixture.

Now referring to FIG. 1A, the bottom end of adapter 22 is positioned on storage bottle 24 with the aid of o-ring 23 to help seal the adapter 22 connection to the storage bottle 24. Pump head 18 is positioned on the top end of adapter 22. Now referring to FIG. 1B, as in FIG. 1A, adapter 22 is positioned onto storage bottle 24 using o-ring 23 to help seal the adapter 22 connection to the storage bottle 24. Pump head 18 is positioned onto the top end of adapter 22 and outlet guide 26 is positioned onto and supported by pump head 18. Now referring to FIG. 1C, adapter 22 is shown positioned on storage bottle 24, pump head 18 is positioned onto adapter 22 and outlet positioning fixture 20 is positioned onto pump head 18.

Figure 2:
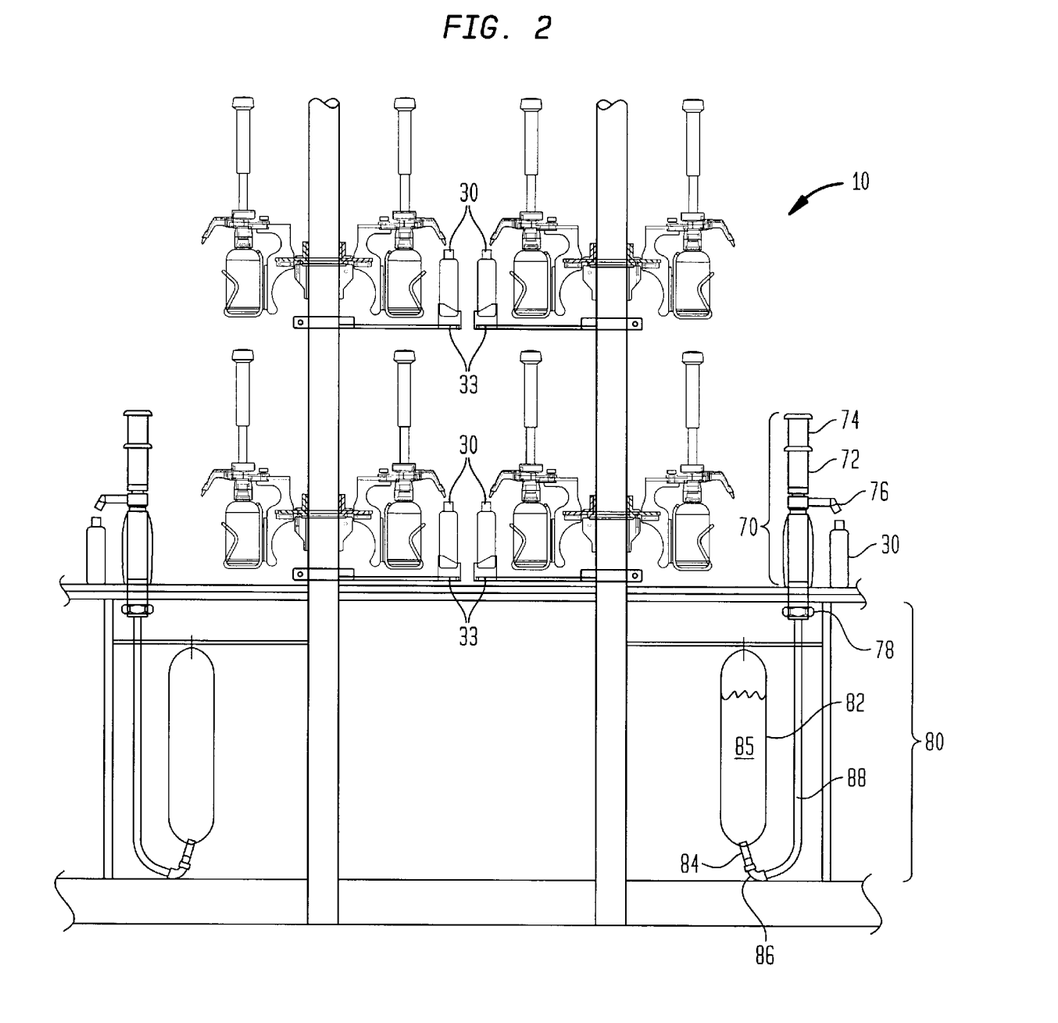
FIG. 2 is a cross sectional view of another embodiment of the inventive dispensing system having a plurality of dispensing devices and storage bottles in a carousal type, over and under arrangement.

Now referring to FIG. 2, four dispensing stations are illustrated, arranged in a carousel like arrangement in two layers. Four consumer bottles 30 are shown positioned in four consumer bottle holders 33 ready to accept customizing agents 21. Also shown are two product base dispensing stations 70 each consisting of product base measuring device 72 and product base pump 74. In operation, product base pump 74 draws product base from product base storage system 80 and dispenses it through product base outlet 76 into consumer bottle 30. In this embodiment, product base 85 is typically dispensed into consumer bottle 30 before customizing agents 21 are dispensed into the same container, although this procedure may be altered as desired. Product base storage system 80 comprises product base storage tank 82 containing product base 85. Product base 85 flows through product base storage tank outlet 84, through product base storage tank adapter 86 and into one end of product base storage tank hose 88, which is connected at its other end to product base dispensing station 70 via product base adapter 78.

Figure 3:
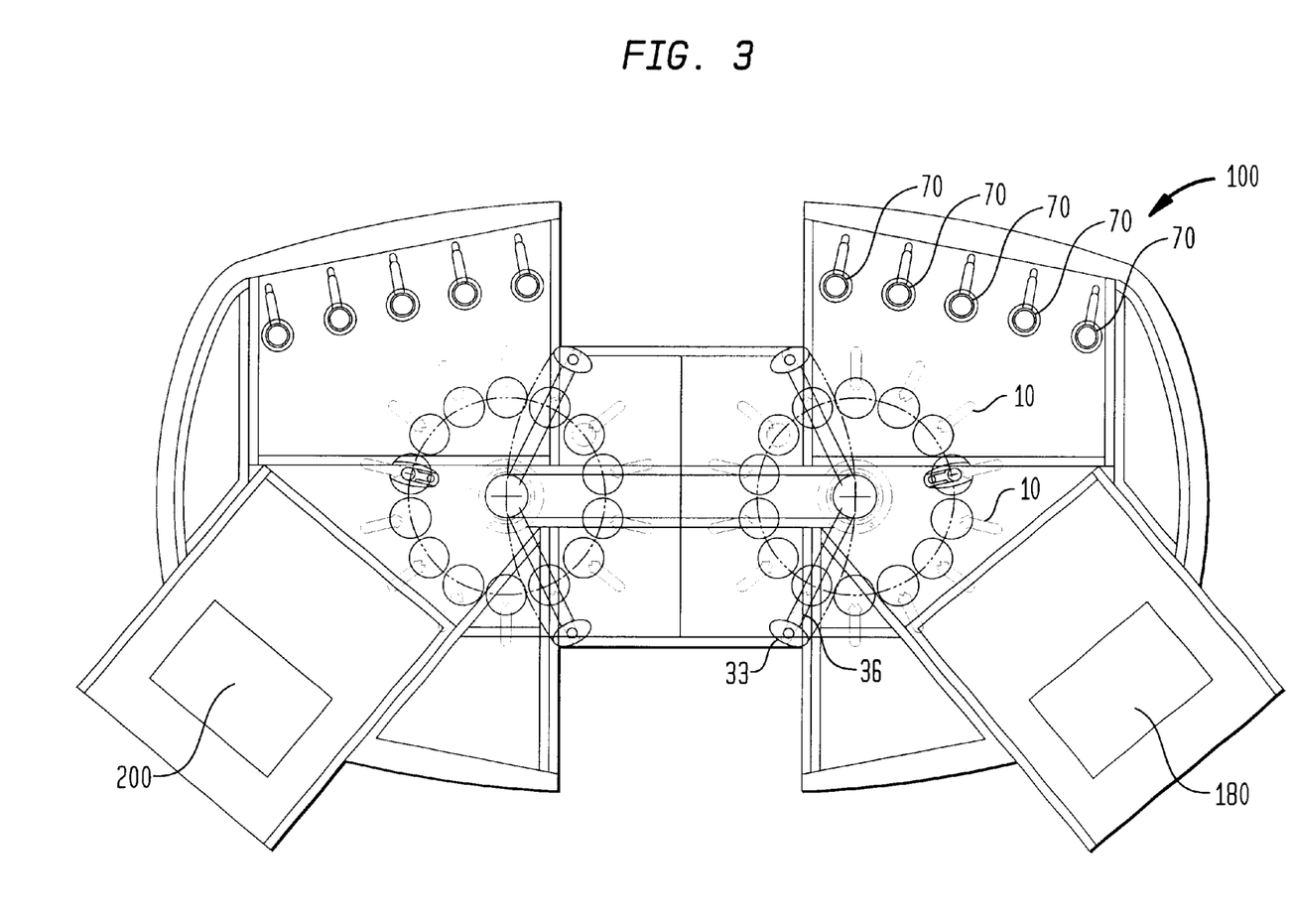
FIG. 3 is a top planar representation of the same embodiment of the inventive dispensing system illustrated in FIG. 2. Also illustrated is the labeling device and external-mixing device.

Now referring to FIG. 3, a plurality of dispensing stations 10 are shown positioned on a carousel type platform. Also shown, are a plurality of consumer bottles 33 each positioned at one end of a corresponding plurality of consumer bottle holding supporting members 36. Also shown in close proximity to dispensing station 10 are a plurality of product base dispensing stations 70, external mixing device 180, and labeling device 200.

Figure 4A:
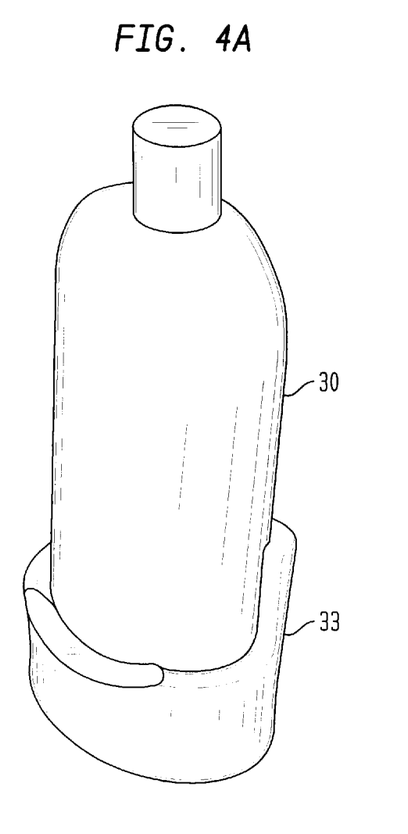
FIG. 4A is a perspective representation of the consumer storage bottle positioned in a consumer bottle holder in the embodiments depicted in FIGS. 1 and 2.
Figure 4B:
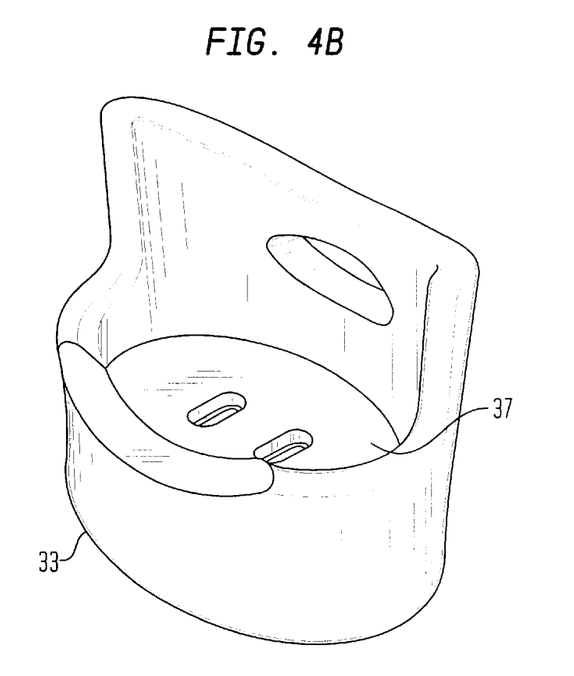
FIGS. 4B and 4C are perspective representations of consumer bottle holder from above and below respectively which is depicted in FIG. 4A.
Figure 4C:
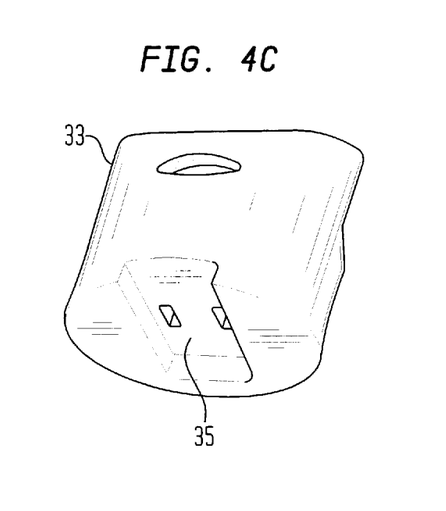

Now referring to FIG. 4A, consumer bottle 30 is shown positioned in consumer bottle holder 33. Now referring to FIGS. 4B and 4C, consumer bottle holder 33 is illustrated from above and below respectively. Also depicted in FIG. 4C, is consumer bottle holder locating channel 35 situated on the bottom of consumer bottle holder 33. Also shown in FIG. 4B is consumer bottle holder aperture 37, which receives consumer bottle 30.

Figure 5A:
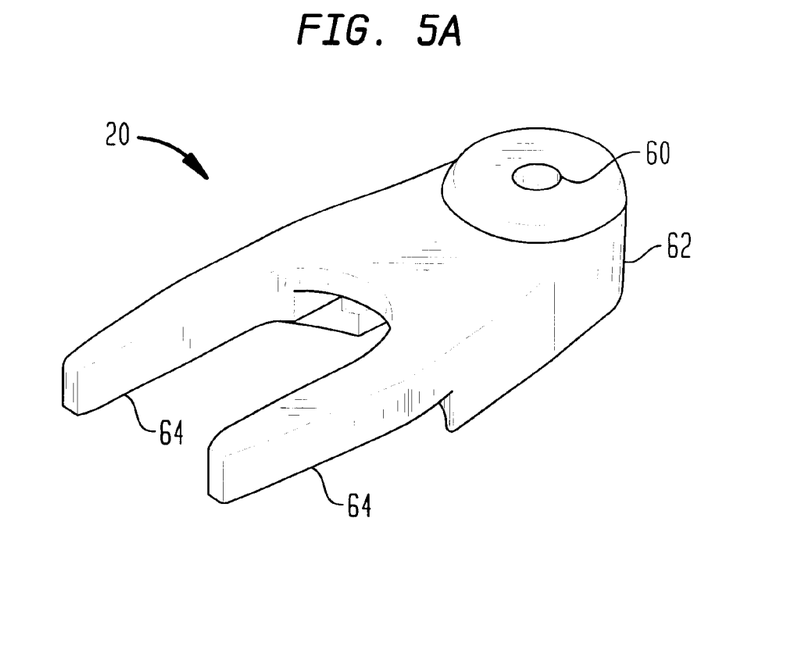
FIGS. 5A and 5B are perspective representations of the outlet positioning fixture from above and below respectively which used in the embodiments depicted in FIGS. 1 and 2.
Figure 5B:
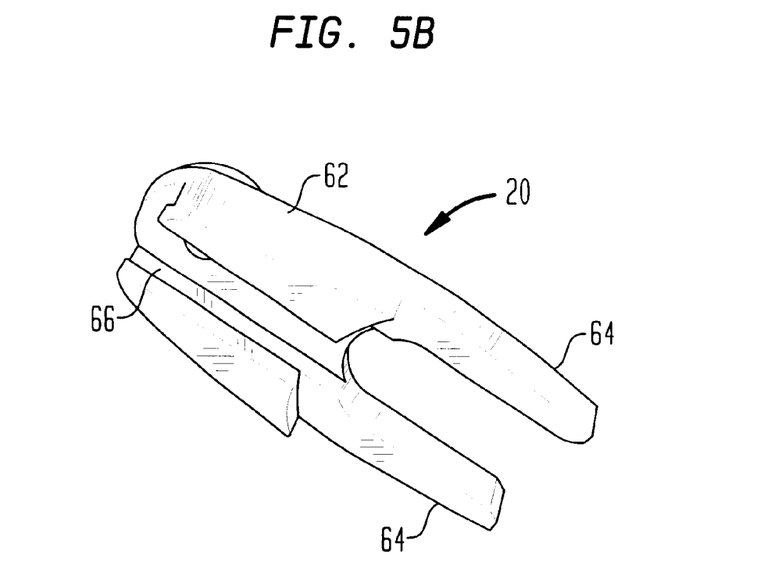

Now referring to FIGS. 5A and 5B, outlet positioning fixture 20 is shown from above and below respectively having outlet positioning fixture body 62 and outlet positioning fixture arms 64. In FIG. 5A, outlet positioning fixture fastener aperture 60 is shown. In FIG. 5B, outlet positioning fixture locating channel 66 is illustrated, which slidably engages both pump head 18 and outlet guide 26 preventing outlet guide 26 from rotating so that it remains in alignment with consumer bottle 30 when positioned in consumer bottle holder 33.

Figure 6A:
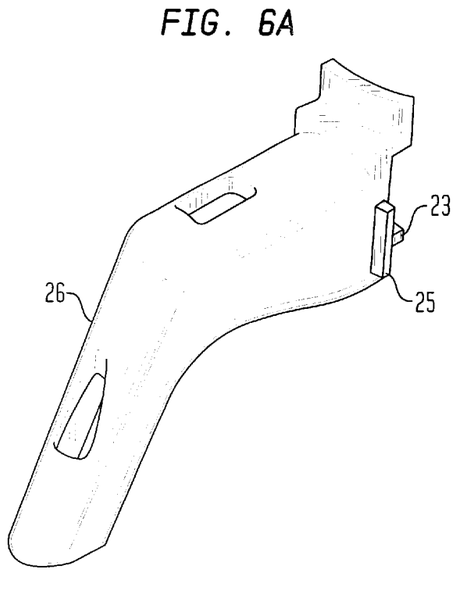
FIGS. 6A and 6B are perspective representations of outlet guide from above and below respectively which used in the embodiments depicted in FIGS. 1 and 2.
Figure 6B:
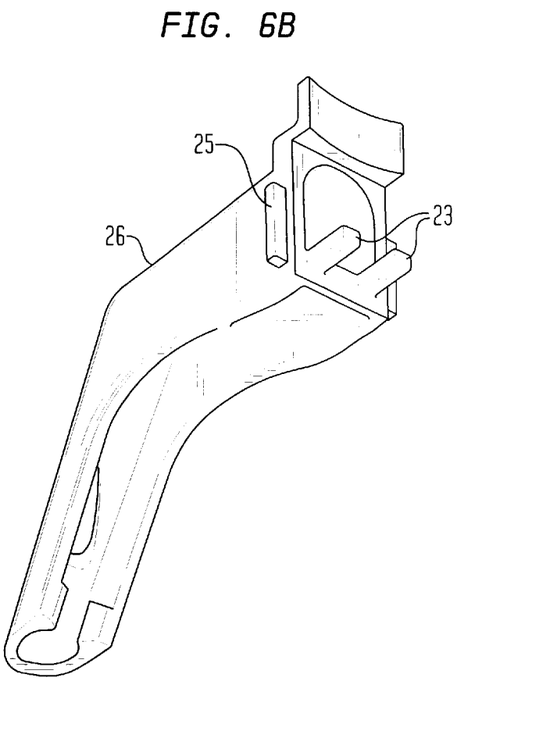
Figure 6C:
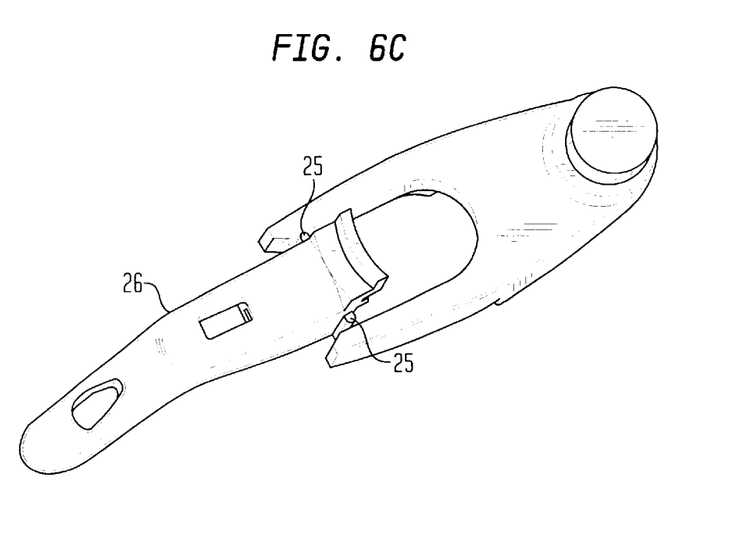
FIG. 6C is a perspective representation of the outlet guide depicted in FIGS. 6A and 6B engaged in the outlet positioning fixture depicted in FIGS. 5A and 5B.

Now referring to FIGS. 6A and 6B, outlet guide 26 is shown, from above and below respectively, having outlet guide positioning members 23 which engage complementary apertures (not shown) in pump head 18 so that outlet guide 26 is properly aligned with pump head 18. Outlet guide flanges 25 are fixedly attached to outlet guide 26. Now referring to FIG. 6C, outlet guide 26 is removably engaged in outlet positioning fixture 20, and in pressing engagement with outlet positioning fixture arms 64 which are biased to hold outlet guide flanges 25.

Figures 7A, 7B, 7C:
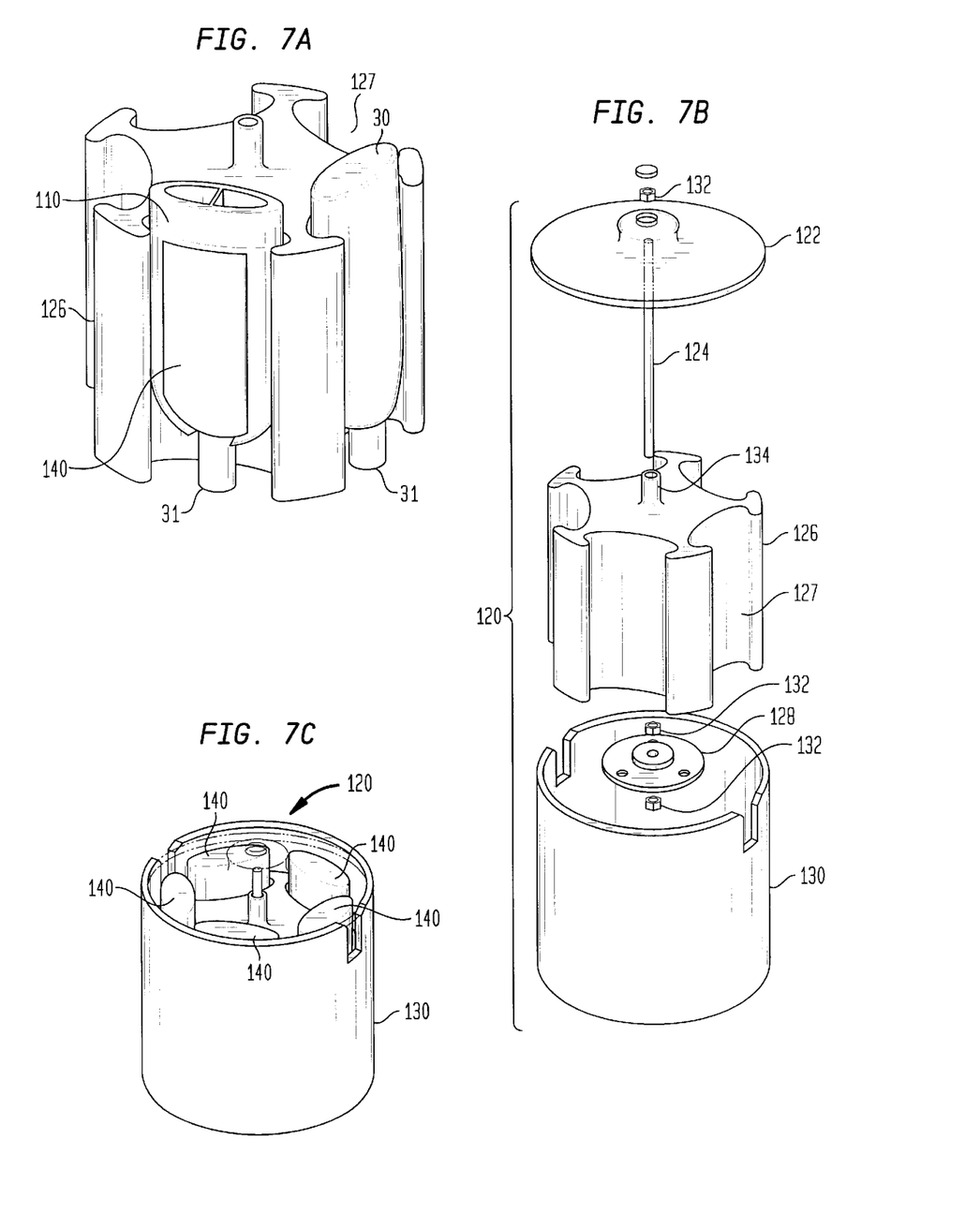
FIG. 7A is a perspective representation of bottles contained in a bottle holder.
FIG. 7B is an exploded diagram of the bottle holder being received into a bottle holder container.
FIG. 7C depicts the bottle holder and its container illustrated in FIG. 7B assembled.

FIG. 7A illustrates consumer bottle mixer holder 126 containing at least one consumer bottle 30, having consumer bottle cap 31, positioned in consumer bottle mixer sleeve 110. The combination of consumer bottle 30 and consumer bottle mixer sleeve 110 is illustrated as consumer bottle and sleeve assemby 140. Depending on the size of consumer bottle 30, the bottle may be positioned in consumer bottle mixer holder 126 without an adapter 110, or it can be positioned with the adapter 110 if the bottle 30 is too small to fit into the consumer mixer bottle seat 127, sized to contain consumer bottle mixer sleeve 110.

Now referring to FIG. 7B, consumer bottle mixer holder 126 is shown being received in consumer bottle mixer assembly holder 130. Also shown is consumer bottle mixer assembly cover 122, positioned onto consumer bottle mixer assembly shaft 124 being received into consumer bottle mixer holder 126 via consumer bottle mixer holder channel 134, and secured by consumer bottle mixer assembly shaft retaining ring 128 and threaded fasteners 132.

Figure 7D:
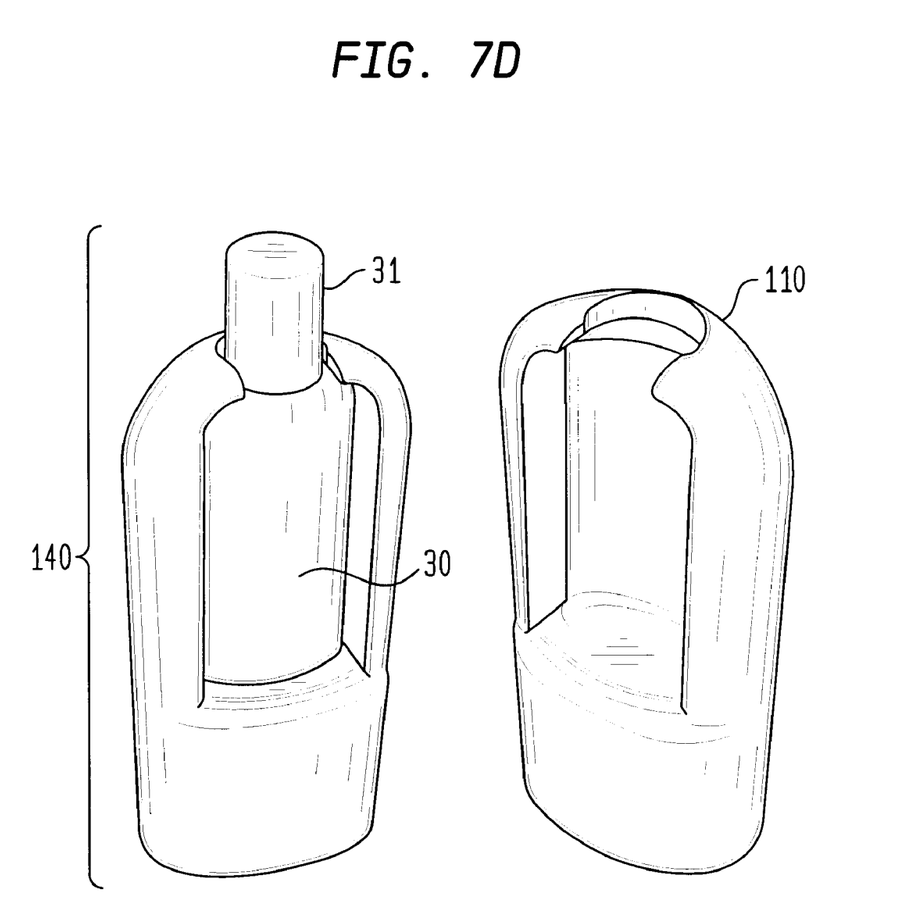
FIG. 7D is a perspective representation of a consumer bottle in an adaptor sized to fit into the bottle holder depicted in FIGS. 7A, 7B, and 7C. Also depicted is a perspective representation of the adapter without the bottle.

Now referring to FIG. 7C, consumer bottle mixer assembly 120 is illustrated in an assembled positioned with consumer bottle mixer holder 126, containing 5 consumer bottle and sleeve assembly units 140. Now referring to FIG. 7D, consumer bottle 30 is shown in pressing engagement with consumer bottle mixer sleeve 110 sized to fit into consumer bottle mixer holder 126 depicted in FIGS. 7A, 7B, and 7C. Also depicted is consumer bottle mixer sleeve 110 without the bottle.

DETAILED DESCRIPTION OF THE INVENTION

In one aspect of the invention is an apparatus for providing a customized, personal care product to a consumer at a location remote from a second location in which a personal care product base is prepared, comprising:

a. a plurality of measuring devices for determining amounts of at least one of said product base and a plurality of customizing agents to be blended into a container;

b. a plurality of dispensing devices, each fluidly communicating with one of said measuring devices, for dispensing said amounts of at least one of said product base and a plurality of customizing agents into said container;

c. an external mixing device for blending said product base and customizing agents after being dispensed into said container by agitating said container; and d. a labeling device for labeling said container with only the ingredients contained in the custom blended product.

In another aspect of the invention is a kit for providing a customized, personal care product to a consumer at a location remote from a second location in which a personal care product base is prepared, comprising:

a. a plurality of measuring devices for determining amounts of at least one of said product base and a plurality of customizing agents to be blended into a container;

b. a plurality of dispensing devices, each fluidly communicating with one of said measuring devices, for dispensing said amounts of at least one of said product base and a plurality of customizing agents into said container;

c. an external mixing device for blending said product base and customizing agents after being dispensed into said container by agitating said container; and d. an external-labeling device for labeling said container with only the ingredients contained in the custom blended product.

Preferably, the plurality of dispensing devices are situated in a carousel arrangement having at least two layers of devices oriented in an over and under relationship defined by an arc. Preferably, the dispensing devices are each supported by a holding device and an outlet positioning fixture. Preferably, the holding device and the outlet positioning fixture are attached to a dispenser supporting member on a first end; and the supporting member, on its second end, is rotatably coupled to a shaft positioned at the center of the arc, and the shaft is oriented perpendicular to the plane of the arc. Preferably the holding device or container holder is slidably attached to said dispenser supporting member for adjusting the outlet's vertical position in relation to the consumer bottle. More preferably, the dispensing and measuring devices are removable as a single unit, thus facilitating the replacement and replenishment of performance and customizing agents, and the prevention of contamination.

Preferably the apparatus or kit has a plurality of dispensing devices with at least one storage container for containing product; at least one measuring device for measuring product to be dispensed; at least one adaptor for removably coupling said measuring device to said container; and at least one pump fluidly communicating with the measuring device for dispensing measured product. Especially preferred is the arrangement where the final product volume may be pre-selected and does not vary for any number of customizing agent variants for a single product form, preferably not in excess of three variants.

Preferably the measuring device has at least one outlet for dispensing product; at least one inlet for admitting air to replace dispensed product.

Preferably the outlet is oriented in a fixed direction with an outlet-locating fixture along a radius of the arc. More preferably, the outlet positioning fixture is a yoke assembly slidably attached to the dispenser supporting member to position said outlet along the radius of said arc.

Preferably, the apparatus or kit has a container holder and a container supporting member having a first end and a second end; whereby the container holder is positioned so that said container may be placed in said holder and reproducibly positioned to receive the product dispensed through said outlet. Preferably the container holder is attached to the first end of the container-supporting member; and the container-supporting member is attached on the second end to the shaft. More preferably, the dispenser supporting member is rigidly attached to a bearing collar rotatably coupled to said shaft; and the bearing collar has a detent device for reproducibly positioning one or more dispensing device outlets at a predetermined position along its arc of motion.

Preferably, the inventive apparatus or kit has a holding device which has a biasing member that releasably holds the storage container; and the holding device is slidably attached to the dispenser supporting member so as to adjust the position of the storage container and the outlet along the major axis of the supporting shaft. The holding device may be optionally removable for disassembly and cleaning.

Preferably the inventive dispensing apparatus has a plurality of user stations to allow the simultaneous preparation of customized personal care products.

The mixing motion providing agitation and mixing of product base and customizing agents may be generated by internal or external mixers providing a simple oscillatory or vibrating motion wherein the consumer container with the blended personal product is simply shaken rapidly back and forth through a short distance. Preferably, more advanced mixers are used which provide a gyroscopic motion wherein a container is moved, usually rotated, about one axis while simultaneously being moved, usually spun, about a second axis perpendicular to the first such as is done by the Red Devil twin axis orbital Speed Demon Mixer® available from the Red Devil Equipment Co. (Brooklyn Park, Minn.), or the like. Especially preferred are mixing devices disclosed in U.S. Pat. No. 5,749,652 issued to Brunn, et. al. on May 12, 1998; and U.S. Pat. No. 5,383,163 issued to Brunn, et. al. on Jan. 17, 1995; both here incorporated by reference. Preferably a circular mixing motion having a relatively large diametric (and radial) displacement at a relatively slow speed to mix a viscous fluid, preferably a personal care product, in a short period of time without producing foaming or air entrapment in the fluid. Preferably the displacement and speed is sufficiently large and slow to maintain any air pocket within the container substantially intact and cause it to move within the container along a path which includes both vertical and horizontal components. Accordingly, one aspect of the preferred mixing method of the present invention takes advantage of the air pocket found in the consumer product bottle after filling. However, the mixing advantages of the preferred mixing method can be achieved without an air pocket. Thus, in contrast to mixers that try to achieve mixing by using high-speed oscillatory or vibratory motion over short distances, the preferred mixing apparatus of the present invention accomplishes mixing by using relatively slow speeds and large displacements. This substantially reduces wear and tear on the mixing device and significantly reduces the entrapment of air bubbles in the blended personal care product.

Preferably the internal or external mixer has a container holder that can accommodate a plurality of consumer containers of the same or different volumes, thus increasing productivity.

Preferably, the consumer container has a neck for facilitating the dispensing of a flowable or extrudable personal product. Especially preferred is a threaded or flanged neck for use with a cap (with or without an integrated orifice), or a pump dispenser, which is designed to securely fit on the neck, or the like. Preferably, the consumer bottle is filled with the selected base product, and the selected customizing agents, to a level below the bottle neck, a plug sized to fill at least 50% of the volume of the bottle neck is inserted inside the neck, the bottle is inserted into the mixer holder in a substantially inverted position, and the inverted bottle is agitated until the contents have been uniformly blended. This is done in part to improve mixing efficiency when the container's contents are blended by an external-mixing device. Preferably the container is situated in the mixer in a position at an angle of greater than 10 degrees, more preferably greater than 30 degrees, from its major axis vertical orientation, and most preferably in a position substantially inverted from its filling position. If the bottle is smaller than the mixer holder, the bottle may be slid into a bottle sleeve adapted to fit both the mixer holder and the bottle.

In another aspect of the invention, an internal or external labeling device applies a customized label to the container identifying only the components of the base formula and dosed customizing agents actually contained in the container. The labeling device may produce the label by any suitable means, preferably by a computer interfaced with a printer which allows for the user to input the consumer's custom product selections and accesses a database of ingredients contained in the available product bases and customizing agent compositions to produce a customized label. In another embodiment, the dispensing device may be electronically linked with an internal labeling device by art recognized techniques, so that a signal is sent to the labeling device when such dispenser is activated identifying the component dispensed, and preferably the volume dispensed, so that a custom label is provided identifying only the components actually dispensed into the container.

The same or a different computer printer combination may also be used to insert a code on the label, e.g. a machine readable bar code or the like, capable of tracking the identity of both the product and the consumer for later reference. In this way, the consumer can easily reorder the custom product from the same location the product was purchased or from a remote location. The consumer may also return to the store or kiosk and allow the previous label to be scanned thus facilitating the purchase of additional product.

In another aspect, the inventive apparatus or kit produces custom products of convenient volume to facilitate consumer use. Preferably, the apparatus is designed to accommodate a consumer container for the final product having a volume under about 1 liter, preferably under about 220 mls.

The foregoing description and examples illustrate selected embodiments of the present invention. In light thereof variations and modifications will be suggested to one skilled in the art, all of which are within the scope and spirit of this invention.

We claim:

1. An apparatus for providing a customized, personal care product to a consumer at a location remote from a second location in which a personal care product base is prepared, comprising:
   a. a plurality of measuring devices for determining amounts of at least one of said product base and a plurality of customizing agents to be blended into a container;
   b. a plurality of dispensing devices, each fluidly communicating with one of said measuring devices, for dispensing said amounts of at least one of said product base and a plurality of customizing agents into said container;
   c. a mixing device for blending said product base and customizing agents after being dispensed into said container by agitating said container; and
   d. a labeling device for labeling said container with only the ingredients contained in the custom blended product; and wherein said plurality of dispensing and measuring devices are removable as a single unit.

2. The apparatus of claim 1 wherein said plurality of dispensing devices each having an outlet are situated in a carousel arrangement having at least two layers of devices oriented in an over and under relationship; said layer arrangement defined by an arc; said dispensing devices each being supported by a holding device and an outlet positioning fixture; said holding device and said outlet positioning fixture being attached to a dispenser supporting member on a first end; said supporting member, on its second end, being rotatably coupled to a shaft positioned at the center of said arc, said shaft being oriented perpendicular to the plane of said arc.

3. A The apparatus of claim 2 wherein said outlet is oriented in a fixed direction with said outlet positioning fixture along a radius of said arc.

4. The apparatus of claim 2, having a container holder and a container supporting member having a first end and a second end; said container holder being positioned so that said container may be placed in said holder and reproducibly positioned to receive the product dispensed through said outlet; said container holder being attached to said first end of said container supporting member; said container supporting member being attached on said second end to said shaft.

5. The apparatus of claim 2, wherein said holding device has a biasing member that releasably holds said storage container; said holding device being slidably attached to said dispenser supporting member to adjust the position of said storage container and said outlet along the major axis of said supporting shaft.

6. The apparatus of claim 2, wherein said outlet positioning fixture is a yoke assembly slidably attached to said dispenser supporting member to position said outlet along the radius of said arc.

7. The apparatus of claim 2, wherein said dispenser supporting member is rigidly attached to a bearing collar rotatably coupled to said shaft; said bearing collar having a detent device for reproducibly positioning at least one of said dispensing device outlets at a predetermined position along said arc.

8. The apparatus of claim 7, wherein said container holder is removable from said dispenser supporting member.

9. The apparatus of claim 1, wherein said plurality of dispensing devices each has at least one storage container for containing product; at least one measuring device for measuring product to be dispensed; at least one adaptor for removably coupling said measuring device to said container; at least one pump fluidly communicating with said at least one measuring device for dispensing measured product; at least one outlet for dispensing product; and at least one inlet for admitting air to replace dispensed product.

10. The apparatus of claim 1, wherein said mixing device is a twin axis orbital mixer.

11. The apparatus of claim 1, wherein said mixing device simultaneously agitates said containers having different volume capacities.

12. The apparatus of claim 1 wherein a final product volume may be pre-selected and does not vary for said customizing agent variations for a single product form.

13. A kit for providing a customized, personal care product to a consumer at a location remote from a second location in which a personal care product base is prepared, comprising:

(a) a plurality of measuring devices for determining amounts of at least one of said product base and a plurality of customizing agents to be blended into a container;

(b) a plurality of dispensing devices, each fluidly communicating with one of said measuring devices, for dispensing said amounts of at least one of said product base and a plurality of customizing agents into said container;

(c) an external mixing device for blending said product base and customizing agents after being dispensed into said container by agitating said container;

(d) an external-labeling device for labeling said container with only the ingredients contained in the custom blended product; and wherein said plurality of dispensing and measuring devices are removable as a single unit.

* * * * *